(12) United States Patent
Carnevali et al.

(10) Patent No.: US 10,293,011 B2
(45) Date of Patent: May 21, 2019

(54) COMPOSITION COMPRISING NATURAL SUBSTANCES HAVING HEALING, REPELLENT AND BIOCIDAL PROPERTIES FOR THE TREATMENT AND THE CURE OF EXTERNAL WOUNDS

(75) Inventors: Fiorella Carnevali, Viterbo (IT); Stephen Andrew Van Der Esch, Rome (IT)

(73) Assignee: PHYTOCEUTICALS LTD., Adliswil (CH)

( * ) Notice: Subject to any disclaimer, the term of this patent is extended or adjusted under 35 U.S.C. 154(b) by 968 days.

(21) Appl. No.: 11/659,028

(22) PCT Filed: Jul. 29, 2005

(86) PCT No.: PCT/IT2005/000454
§ 371 (c)(1),
(2), (4) Date: Jan. 31, 2007

(87) PCT Pub. No.: WO2006/013607
PCT Pub. Date: Feb. 9, 2006

(65) Prior Publication Data
US 2008/0305179 A1    Dec. 11, 2008

(51) Int. Cl.
*A61K 36/53* (2006.01)
*A61K 36/38* (2006.01)
*A61K 36/58* (2006.01)

(52) U.S. Cl.
CPC .............. *A61K 36/53* (2013.01); *A61K 36/38* (2013.01); *A61K 36/58* (2013.01)

(58) Field of Classification Search
None
See application file for complete search history.

(56) References Cited

U.S. PATENT DOCUMENTS 4,318,906 A * 3/1982 Llopart ........................ 424/745
6,126,950 A * 10/2000 Bindra et al. ................ 424/401
6,203,796 B1 * 3/2001 Papaprodromou ........... 424/745
6,241,988 B1 * 6/2001 Erdelmeier et al. .......... 424/730
6,703,034 B2 * 3/2004 Parmar et al. ................ 424/405

FOREIGN PATENT DOCUMENTS

GB          1456275 A    * 11/1976
KR       2003002004      *  1/2003

OTHER PUBLICATIONS

Gregory et al. Comparison of Propolis Skin Cream to Silver Sulfadiazine: A Naturopathic Alternative to Antibiotics in Treatment of Minor Burns. J Altern Complemen Med. Feb. 2002; 8 (1) 77-83).*
Shulz et al. "Rational Phytotherapy: A Physicians' Guide to Herbal Medicine, Fourth Edition". Springer-Verlag: Heidelberg/New York, 2001, p. 59.*
Sathyanaryana et al. (1994) from "Neem: the divine tree, *Azadirachta indica* " by Puri, H.S. Amsterdam: Harwood Academic Publishers, 1999, p. 104.*
Ghandi et al. J Ethnopharmacol. May-Jun. 1988;23(1):39-51. Abstract only.*
Hobbs, C. St. John's Wort. Ancient Herbal Protector. Web copyright date: 1998. pp. 1-5. Retrieved from the internet: <URL: http://www.christopherhobbs.com/website/library/articles/article_files/st_johnswort_02.html[Jul. 25, 2013 11:10:55 PM].>.*

* cited by examiner

*Primary Examiner* — Amy L Clark (74) *Attorney, Agent, or Firm* — Nath, Goldberg & Meyer; Tanya E. Harkins; Scott H. Blackman

(57) ABSTRACT

Compositions of natural substances for human and veterinary use are provided and include neem oil mixed with the oil extract of *Hypericum*. The compositions have healing, anti-bacterial, anti-inflammatory, and pain relieving properties combined with a repellent effect against myiasigenic diptera and non-myiasigenic diptera. The compositions can be used for the treatment and the cure of external wounds of any type and extension.

18 Claims, 6 Drawing Sheets

| DOGS | SORT OF LESIONS | TIME COURSE MIX | START OF MIX THERAPY | SYSTEMIC THERAPY | LOCAL THERAPY | DAYS OF INFLAMMATION |
|---|---|---|---|---|---|---|
| Face off | Lacerated and contused wound at Head, neck and right ear | 4 months | from onset | antibiotic for 1 week | Failed surgical reconstruction | 3 |
| Legs | Traumatic wound of the upper part of fore legs | 20 days | from onset | antibiotic for 1 week | Rinsing with saline solution | 3 |
| Tail | Necrosis of the tail stump | 20 days | from onset | antibiotic for 1 week | Rinsing with saline solution | 3 |
| Lilla | Traumatic wound ear neck and shoulder | 25 days | from onset | antibiotic for 1 week | Maggotts removal and rinsing | 3 |
| Ross | Traumatic removal of one of the anterior cushion | 30 days | from onset | antibiotic for 1 week | Surgical reconstruction | 5 |
| Pablo | Perianal fistula and rhagades | 20 days | chronic lesion | none | Rinsing with saline solution | 7 |
| Bedsore | Bed sore at elbow | 20 days | chronic lesion | none | none | 0 |
| Shoulder | Lacerated and contused wound at shoulder | 20 days | from onset | none | none | 0 |
| Prolapse1 | Prolapse of the rectum | 3 days | after 2 days | none | clyster with mix | 1 |
| Prolapse2 | Prolapse of the rectum | 5 days | after 2 days | none | clyster with mix | 2 |

Figure 9

| | SORT OF LESIONS | TIME COURSE MIX | START OF MIX THERAPHY | SYSTEMIC THERAPY | LOCAL THERAPY | DAYS OF INFLAMMATION |
|---|---|---|---|---|---|---|
| ALPACA | | | | | | |
| All | Purulent fistulae and abscesses at different parts of the body | 30 days | chronic lesion | none | iodine rinsing | 20 |
| GOATS | | | | | | |
| Saanen | Purulent abscesses caused by Corinebacterium pseudotubercolosis | 30 days | chronic lesion | none | iodine rinsing | 7 |
| SHEEP | | | | | | |
| Hoofs (15) | Infested wounds at the hoofs by maggots of Wolphartia magnifica | 15-20 days | chronic lesion | none | Maggotts removal and rinsing | 7 |
| Foreskin (3) | Infested wounds at the foreskin by maggots of W. magnifica | 15-20 days | chronic lesion | none | Maggotts removal and rinsing | 0 |
| Head | Infested wounds at the top of the head by maggots of W. magnifica | 33 days | chronic lesion | none | Maggotts removal and rinsing | 0 |
| Side | Necrotic wound at the flank infested by maggots of Wolphartia magnifica | 41 days | chronic lesion | none | Maggotts removal and rinsing | 4 |
| Tail | Necrotic wound at the tail infested by maggots of W. magnifica | 17 days | chronic lesion | none | Maggotts removal and rinsing | 0 |
| BOVINE | | | | | | |
| Cow | Sore caused by flange of the ruminal fistula | 30 days | after 20 days | none | none | 0 |
| PORCUPINE | | | | | | |
| hedgehog | Traumatic wounds of the hind part of the body | 30 days | after 7 days | antibiotic for 1 week | Failed surgical reconstruction | 7 + 5 |

Figure 10

| HORSES | SORT OF LESIONS | TIME COURSE MIX | START OF MIX THERAPY | SYSTEMIC THERAPY | LOCAL THERAPY | DAYS OF INFLAMMATION |
|---|---|---|---|---|---|---|
| Asino | Lacerated and contused wound at the hide part of the body caused by dog bites | 4 months | after 7 days | none | injection of mix in the cavities | 7 + 5 |
| Principessa | Purulent abscess at the neck | 1 month | after 7 days | antibiotic for 3 weeks | Rinsing with saline solution | 7 + 4 |
| Vispo | Traumatic abscess at intermandibular space | 1 month | from onset | antibiotic for 1 week | none | 3 |
| Larynx Operation | Second intention healing of surgical wound at the larynx | 15 days | from onset | antibiotic for 2 weeks | none | 0 |
| Marat | Ventral abscesses | 1 month | from onset | antibiotic for 2 weeks | Rinsing with saline solution | 4 |
| Zerdiana | Traumatic wound right shoulder | 8 months | after 20 days | antibiotic for 2 weeks | none | 0 |
| Stephan Grigio | Traumatic wound hind part of the elbow | 54 days | from onset | antibiotic for 1 week | none | 0 |
| Avelignese | Traumatic wound at left carpus region | 20 days | after 7 days | antibiotic for 1 week | Rinsing | 7 + 3 |
| Sudan | Traumatic wound at right carpus region | 3 months | after 7 days | antibiotic for 1 week | Partial surgical reconstruction | 0 |
| Drago | Traumatic wound at both carpus regions | 51 days | from onset | antibiotic for 1 week | compared therapy with traditional | 0 |
| Riano | Traumatic wound at left tarsum region | 5 months | after 4 months | none | permanent rinsing with saline solution | 4 months + 20 |
| Tommaso | Small wound at the medial part of the shin-bone | 1 month | after 5 days | none | none | 0 |
| Saura di Sutri | Traumatic wound at the hind shin-bone (cheloid) | 3 months | after 7 days | none | Rinsing with saline solution | 0 + 5 |
| Manlio | Small wound at the anterior part of the shin-bone | 70 days | after 2 weeks | none | none | 0 |
| Sabina | Small button-like wounds at the hind shin-bones | 40 days | after 2 weeks | none | none | 0 |
| Comand Quir | Traumatic wound at posterior metatarsum | 3 months | after 30 days | none | none | 0 |
| Eddy | Traumatic wound at the fetter region (cheloid) | 48 days | after 2 weeks | none | none | 0 |
| Linotte | Traumatic wound at the anterior part of the posterior fetter region | 4 months and 12 days | from onset | none | none | 0 |
| Unno | Chronic wound (cheloid) at the anterior part of the posterior fetter region | 4 months and 10 days | chronic lesion | none | none | 0 |
| Sardo Nuovo | Small wounds at the flank | 2 weeks | from onset | sudden | none | 0 |
| Seafield Clover | Small wounds at the gluteus | 3 weeks | from onset | sudden | none | 0 |

Figure 11

COMPOSITION COMPRISING NATURAL SUBSTANCES HAVING HEALING, REPELLENT AND BIOCIDAL PROPERTIES FOR THE TREATMENT AND THE CURE OF EXTERNAL WOUNDS

The present invention relates to the field of medical devices and in particular to a composition comprising natural substances, of plant origin, that can be used for the treatment and the cure of external lesions, of any nature, which combines, at the same time, healing, antiseptic, anti-bacterial, repellent towards myiasigenic diptera and non-myiasigenic diptera, anti-inflammatory and pain relieving properties.

As well known in the art, usual protocols for the therapy of external wounds, in human and in veterinary medicine, include the steps of curettage (removal of soft parts in ischemia, necrotic or degenerative, or suppurative) followed by disinfection with disinfectants containing either Iodide or benazachil-chlorides or compounds based on hydrogen peroxide, these disinfectants are variably tissue-damaging, but are considered indispensable to remove or kill bacterial species infecting the lesions. In a further step an antibiotic therapy is applied, locally or systemically, under the form of powder, cream, liquid or spray formulations, in order to further prevent and/or contrast bacterial infection, even if it is partially tissue damaging and does not favour healing. At the end, in order to maintain the lesions soft and to avoid hardening and dehydration of crust, especially in extended lesions or burn wounds, gauzes soaked in fatty humefactants based on Vaseline or silicone oils (very expensive) are applied. During the maintenance therapy, the above mentioned remedies are applied when necessary, awaiting for the spontaneous activation of the healing (reparation) processes. In particular, secretions and exudations, more or less copious depending on the nature and the extension of the wound, are daily removed followed by disinfection and application of the above mentioned remedies. Optionally, in adequate hygienic/environmental conditions, wounds are protected by bandaging that need to be removed at regular intervals, depending on the nature of the lesion, to avoid numbness, infection or putrefaction of the sore.

In poor hygienic/environmental conditions, i.e. those frequently present in developing countries or in veterinary medicine, often the wounds can not be managed adequately and they remain exposed to attacks of myiasigenic flies (sarcophagidae, callyphoridae) or any other flies (muscidae) which may contribute to important infections of the wound.

A widespread, but inefficient and dangerous, zootechnical practice is to pour Creolina (containing phenols and tar) onto the wounds of animals in order to keep flies away. This remedy, very diffuse and entrenched in animal husbandry, is extremely tissue damaging as well as toxic. Moreover, the repellent effect against flies doesn't exceed half an hour after the treatment and necrotizes and destroys the healing tissues. This remedy can not be used on very extended lesions because of it's extreme toxicity by absorption and of it's tissue damaging properties.

A further remedy, adopted in the zootechnical sector, provides the application of various insecticides, including natural and/or synthetic pyrethroids, that have a larvacidal effect instead of a repellent effect, directly on the maggot infested wounds or sores. The absorption of insecticidal compounds by the open surfaces of wounds may lead, especially in the case of extended and slow-healing lesions, to acute or chronic intoxication of the animals. Furthermore, the arbitrary use of insecticides exposes, on the one hand, the operators to intoxication risks and on the other hand it increases the toxic burden both on the environment as well as on the value added chain of the agro-food sector if the treated animals are directly or indirectly destined for food production.

In the state of the art no medical devices, adopted by official medicine, showing recognised and/or proven healing properties are known.

In veterinary medicine, external wounds (lesions) represent a very difficult problem to manage, especially during the period when flies are active, and in the case of large working animals like mules, horses and donkeys and also for other animals of zootechnical interest (bovines, ovines etc. . . . ) or pet animals of both large and small size.

Even in humans, the management of external wounds (lesions, sores) represents a serious problem in the developing countries where the environmental and hygienic conditions are very often completely inadequate and the risk to be exposed to complications due to parasites, bacteria etc. infections is very high and frequent, especially for weak and undernourished subjects.

The present invention provides a composition comprising neem oil and oil extract of St John's wort (*Hypericum perforatum*) at variable percentages, between 10 and 50%, according to the necessity of obtaining different prevalent effects belonging to the different single components. The neem oil is in a percentage between 10% and 50% and the oil extract of *Hypericum perforatum* is in a percentage between 10% and 50%.

Further characteristics of the present invention are described in the following detailed description of the invention and in the attached figures, where.

The table in FIG. 9 illustrates the results of clinical experimentation carried out on dogs.

(In the first column the single case is identified by the lesion or by the name of the animal, in the second column is summarised the sort of lesion, in the third column in indicated the time course, in the forth column is indicated when the therapy started, in the fifth column is indicated if a systemic therapy was administrated, in the sixth column is indicated the locally therapy used and in the last column is indicated the days of inflammation.)

The table in FIG. 10 shows the results of clinical experimentation carried out on alpaca, goats, sheep, bovine and porcupine.

The table in FIG. 11 shows the results of clinical experimentation carried out on horses.

The present invention discloses a complete therapy for external lesions (wounds) which does not necessitate of any auxiliary therapeutic means i.e. antibiotics, disinfectants, humidifiers, protective means etc. Said medical device can be used, in all circumstances, especially in those where it is impossible to hospitalise the patients in protective conditions, and in all those cases of altered healing processes due to metabolic illnesses or chronic invalidating illnesses.

The technical problem is solved providing a composition comprising the following active compounds: neem oil, having healing, repellent, antiseptic and anti-inflammatory properties and the oil extract of *Hypericum* having healing, lenitive and antiseptic or antibiotic properties.

Patent No. US006113907A discloses clinical studies of St. John's Wort, Mild to moderate depression, antiviral activity, wound-healing effects (wherein antibacterial activity is described) and miscellaneous effects.

Patent No. US00621950A describes an ointment including, among other plant extracts, neem extracts that are used because of it's natural healing properties for cracked skin.

In patent No. KR2003002004 a cosmetic composition containing anti-microbial neem oil is disclosed.

Patent application N. WO 02/22147 describes an antibacterial combination which comprises neem plant extracts.

Patent No. US006579543 states that Neem can be considered as one of the best healing and disinfectant agents for skin diseases. It describes that Neem can be also used as an anti-inflammatory for joint and muscle pain while *Hypericum* treats many ailments, including cuts, grazes, bruises, minor burns, sciatica, injured nerves, inflammations, ulcers, poisonous reptile bites, kidney and lung ailments, allergic reactions, anxiety and depression.

The neem oil is obtained either through cold/heat assisted pressing or through solvent extraction from the mature seeds from the neem tree (*Azadirachta indica* (A. Juss)). The oil obtained is monitored for the absence of mycotoxins (aflatoxins).

The oil extract of St John's wort (*Hypericum perforatum*) is obtained through a maceration process of at least three too six weeks under the sun of the flowered crowns of St John's wort in plant derived oil contained in clear glass recipients. The flowered crowns must be collected at the moment of maximum maturation. After the maceration process is complete the oil extract takes on the typical ruby red coloration. Subsequently the oil extract is filtered and stocked in dark glass recipients in order to avoid oxidative degradation processes due to exposition to natural light or ultraviolet rays. This particular procedure of preparation of the *Hypericum* oil extract guarantees the it's efficacy.

In a further embodiment of the present invention, Azadirachtin A (triterpenoid of the limonoid class which is classified as belonging to the IVth class of toxicity both for the EPA (USA) and the EEA (UE) i.e. not harmful to health or the environment) is added in order to enhance the biocidal effect.

Optionally Azadirachtin A may be added in order to enhance the biocidal effect. Azadirachtin A has insecticidal, growth regulating inhibiting (GRI) and antifeedant properties on many different harmful insect species.

Azadirachtin A is added in a concentration between 100 ppm and 1000 ppm.

Additionally, essential oils of rosemary, basil and oregano can be added antioxidants, preservatives and aromatics.

A solid formulation can be obtained adding to the above described mixtures natural bees wax.

Bees wax, as emulsifier and solidifying agent, is added in a percentage between 7% and 15%.

Olive oil or other commercial seed oils can be added to bring the final solution to 1000 gr.

The single components of the invention are commercially available on the market.

As demonstrated in the following experimental tests the composition, object of the invention, shows in combination all the necessary properties needed to obtain a successful healing of wounds i.e. healing effect, repellent effect, anti-inflammatory effect, lenitive effect and antiseptic effect. The properties of each component are enhanced in comparison to the single plant components, thanks to the synergic effect.

In addition, it represents a single medical device showing disinfectant, anti-inflammatory, anti-microbial, lenitive, analgesic, etc. properties in combination with properties necessary to obtain an efficient healing (trigger, potentiate and accelerate the physiological processes at the base of wound healing) and a repellent effect versus myiasigenic or non-myiasigenic flies.

The composition of the present invention, may be applied daily on the wound surfaces, as a single remedy, also in cases of medium to serious loss of substance i.e profound wounds, lacerated and contused (bruised) with underlying tissues, either destroyed or necrotic or/either suppurating, in substitution of all other remedies actually used.

In conclusion, the composition, object of the present invention, permits to solve the healing of external wounds, of whatever kind and extension, through the speeding up and strengthening of the healing process, without the use of a local antibiotic treatment, (with exception of a systemic antibiotic treatment to be carried out during the initial phases of the activation of the wounded surface protection given by the granulation tissue) and confers an additional protection against myiasigenic or non-myiasigenic flies, which may colonise sores or external wounds both in human as in animal, through its repellent effect.

The experimental results (FIGS. 1A, 1B, 2A, 2B, 3A, 3B, 4A, 4B, 5A, 5B, 6A, 6A, 9, 10, 11) demonstrated an immediate stimulation of the physiological granulation with precocious re-vascularisation of the damaged tissue, elimination of ischemic and necrotic tissues, arrest of serum exudates (called white hemorrhage in case of extensive burning wounds), re-absorption of heamatic spilling and arrest of putrefying bacteria proliferation. After 24-36 hours from the first treatment the wound shows the typical positive reaction aspect of the activated mending process. Moreover, the hurt surface is completely covered with soft, elastic and adequately humidified, granulation tissue, the wounds don't form a permanent hard crust as the serum exudate is stopped. In addition, because of proper humidity, no fissures or cracking of the crust occur. Wounds treated with the composition of the present invention, immediately present a soft and elastic aspect of the damaged parts and no fissuring due to desiccated exudates, that usually is formed on the wound surface under reparation. Daily medication is facilitated, especially in very pain sensitive species i.e man, horse, etc. as a result of the outstanding lenitive and painkiller properties of the invention.

Wound Healing Processes

Wound healing is a complex sequence of cellular and biochemical events. It is a regenerative system for the restoration of the anatomy and the functionality of injured tissues. It is not a complete regenerative system because the final scar does not present the same anatomy and function of the original tissue situation. Therapeutic tools used in wound repairing can be traditional, natural or highly technological. It is known in the scientific field that a single exogenous agent able to effectively mediate all the numerous aspects of the wound-healing process is not available and special omnicomprehensive moisture for the regulation wound-healing processes do not exists.

The healing process consists of 3 phases:

The inflammatory phase: it lasts no more than 3 days but it is prolonged and exacerbated when bacterial infection is present.

The granulation-phase: it starts immediately after injury but becomes evident 3 days after injury. It represent a temporary self-sealing barrier until re-epithelialization of the new skin is complete. It is inhibited or delayed by inflammatory events. It presents different time-courses depending on the species. For most animals and humans, it lasts 15 days, in horse the time-course is very slow (months) depending on the extension, localisation and tension of the wounds. In horses this process may also lead to the pathologic process named cheloid formation.

The remodelling phase: it is the non stable part of the healing process and lasts months or years. It starts when re-epithelialization of the injured part is complete and is responsible for the disfiguring retraction of the scar, when precedent phases are not well regulated.

Anti-Microbial Effect

Bacterial complications (infection) of the wounds always occur, in fact, damaged tissue are colonized immediately after the injury, especially in traumatic wounds contaminated by earth, hair, faeces or provoked by bite.

Has been observed that when the composition, object of the invention, is applied immediately after the injury, the healing process starts without bacterial complications, the inflammatory phase lasts the physiologic 3 days after which granulation tissue becomes evident on all wound surfaces. If the treatment with the composition, object of the invention, begins when bacterial complication and excessive inflammatory reaction are already present, has been regularly observed, within 3 days, the sterilisation of the wounds and the regular transformation of the inflammatory phase in the granulation process due to the antibacterial, anti-inflammatory and healing effects of the composition.

All these effects has been also observed in very complicated wounds of more than 7 days of age (before treatment was initiated), in which gangrenous necrosis on all wound surfaces is present. After 3-5 days from the treatment with the composition object of the present invention, the local and general signs of infection (bad smelling necrosis of wounds, debris, fever, toxemia, etc) disappear.

Effect on Unviable Tissue

In presence of unviable, necrotic and/or infected tissues, saline debridment for the first 2 or 3 days is regularly associated to the treatment with the composition object of the present invention. Saline debridment removes fibrin which trap the necrotic debris and de-hydrates the necrotic tissues which can be removed. Usually this debridment method is not yet sufficient to separate the viable surface from the necrotic tissues, it is slightly painful and provokes hemorrhage from the wound surface. The complete separation of the viable and unviable tissues has to be performed by the activity of the inflammatory cells (especially the "activated macrophages") and the epidermal cells. These two cell lineages, play a very important role in inducing spontaneous debridment of the wounds. The composition, object of the present invention, probably plays a role in recovering and well-regulating these inflammatory and epidermal cells. Has been observed that the mechanical saline debridment method is not completely effective on removing all debris. But before performing the daily debridment, and having treated the wounds surface with said composition the day before, it is possible to remove the old debris in a very short time (one or two days). In extreme cases surgical debridment can be called for. Within 3-5 days the cleaned surface presents a perfect granulation tissue and the second phase of the healing process is induced. Physiologic parameters of the patients return to normal. Acute pain, provoked by the infection and the inflammation status, disappears. Because the apparition of the granulation tissue attests that infection is over and the inflammatory process is transformed into a well-healing process, the antibacterial, anti-inflammatory and the healing effect of the mixture object of the invention are demonstrated.

Lenitive Effect

Has been demonstrated that the composition, object of the present invention, show a lenitive effect not only indirectly. In fact, it is capable to properly regulate the inflammatory process, also when pain is caused by the sensitive injured nervous fibres (as in burns). Animals that are very sensitive to pain, i.e. horses, can be managed without being sedated even in presence of severe injuries. Animals treated with said composition never show the scratching or compulsive licking behaviour. Experimental experiences confirm the rapid lenitive effect of said composition especially when it is applied on burns.

Anti-Haemorrhagic and Angiogenesis Effect

The composition object of the present invention shows an anti-haemorrhagic effect on wound surfaces when granulation tissue are accidentally damaged, haemostasis is achieved in less than one minute after application.

Moreover, said composition presents potent effects on neo-angiogenesis processes during the formation of the granulation tissue, has been shown that granulation tissue always presents the right vascularisation in every part of the wound starting from the first steps of the process. Neo-angiogenesis is a very important process of the second healing phase, it is stimulated by hypoxia of the injured tissue and by the inflammatory reaction. The newly formed vessels have to support the proliferative granulation tissue. Integrity and permeability of these new vessels are regulated by several functional proteins secreted by inflammatory and Mesenchimal cells (fybroblasts). Has been demonstrated that the composition object of the present invention has a potent effect on vascular function due to its ability to arrest hemorrhage (effects on vessel integrity) and its ability to control the swelling of the wound surface (effects on vessel permeability) which represent one of the most important complications in burn wounds. After risk of infection, the exacerbated vessel permeability of the wound surface (lymphorrea or white haemorragy), when affecting large part of the body, can provoke the death of the patients due to blood concentration (inspissatio sanguinis) and consequent block of the renal function. It is possible to obtain the arrest of the white haemorragy within no more than 3 days, and patients even burned over more than 50-60% of the body surface survive. In view of the powerful effects of said composition on lymphorrea, it should be very important to carry out tests on burns in humans.

It could be also interesting to test the effects of the mixture on the retracting phase of the wound healing. This because has been never observed disfiguring scars also when wounds were very serious while in humans the outcome of burns is always disfiguring retracted scars.

Re-Epithelialization

The edges of the wound, regularly treated with the composition, object of the present invention have always shown re-epithelialization signs due to a rapid and effective endothelial migration and transformation of the underlying granulation tissue in pale, mature, healed tissue, also in the cases where extension of the wound area was very large. Wound area restriction appears linear if the composition is regularly applied and it becomes slower if mixture is not applied. In dogs and horses the effect of a well-modulated process of the collagen maturation in the neo re-epithelialized area of the wound is clearly observable. In fact, while the inner part of the damaged area is still covered by granulation tissue, the re-epithelialized margins close to the wound present signs of retraction which disappear while the wound healing process is going on and disappear completely when the healing process is finished.

The composition, object of the present invention, is able to maintain the wound surface well-hydrated (humectant property) since it never becomes covered with dry, dark and anelastic tissue named "escara" (crust). Escara is the normal reaction of the wound surface to the de-hydration process (which is 20 folds more than the de-hydration grade of the healthy skin). The healing process must be performed under the right grade of hydration, otherwise the functional and structural proteins present in the injured tissue form a sticky mixture which traps and hinders the process. The de-hydrated wound surface is not removed by the inflammatory cells until the healing process is complete. Escara has the function to maintain the right hydration level of the wounds until re-epithelialization is performed. It often becomes hard and anelastic and can undergo fissuration and traumatic removal which can provoke haemorrhagy on the underlying granulation tissue. The absence of the escara in all the cases proves that said composition creates a favourable environment on the wound surface avoiding de-hydration and its collateral effects.

When the composition, object of the present invention, is applied, the final scar, in very large and severe wounds, never shows signs of retraction or fibrosis. Reconstructed skin is soft and elastic almost as the original (physiologically recovered) and presents pigmentation and annexes reconstruction (hair, glands). Those effects are due to the perfectly synchronized sequences of the healing events which are rare and almost impossible to achieve in wounds not treated with the present composition.

Repellent Effect

The treated wounds are not colonised by myiasigenic flies for a time of 24 hours following treatment (repellent effect against oviposition).

The repellent effect of the composition, object of the present invention has been well documented in vivo. Diptera visit the wounds of animals during the entire warm and hot seasons. Muscidae (*Musca domestica*) feed on the body fluids, including those secreted by wounds. They represent a real nuisance and a potential mechanical vector of infection. When part of a wound is treated with the present composition, no flies stay on the treated part, while the non treated part is regularly visited. The effect lasts 6-8 hours. By using the composition, object of the present invention, veterinary wound management, during the seasonal period, becomes possible.

Some Sarcophagide Diptera, known as Myiasigenic Flies (*Wolphartia magnifica, Lucilia sericata*) deposit live larvae on wounds and those larvae eat the tissues of the affected animals. Infected wounds which present necrosis and gangrene are colonized by other Sarcophagidae Diptera (*Sarcofaga emorroidaria*). Myiasis is a very big problem in sheep after shearing, after application of the ear tags and in all cases of traumatic wounds especially of the hoof. Myiasis is also an important problem for all other injured animals during the summer time. A flock of sheep, during two summers, has been managed using the present composition obtaining the reduction of the incidence of the affected animals. In other two flocks the present composition was applied on infested wounds when lesions were discovered. The composition, object of the present invention, shows a potent repellent effect against Myiasigenic flies for 24 hours. No new generations of diptera larvae were found in wounds when the present composition is applied daily. Larvae have to be removed mechanically, but depending on the wound, it is not usually possible to remove all larvae present, but in treated wounds it is not a problem because they die within this period (Biocidal effects of the mixture in vitro tested). The wound-healing process presents the course described before. If a cleaned wound is not medicated within 24 hours, new generations of maggots are always deposited otherwise it will heal regularly.

In Vitro Test for Repellent and Biocidal Effects

In order to illustrate the repellent and biocidal effect of composition of neem oil and oil extract of *Hypericum* both the single components and the composition object of the invention have been tested.

The tests were carried out with *Callyphora* sp. flies, which are a common and widespread myiasigenic agent in cattle, in vitro. For every thesis tested 5 replicas were done.

The following tests were carried out:

repellence versus ovipositing females using meat bits totally immersed in the substances to be tested: water, neem oil, oil extract of *Hypericum*, a 50/50 mix of neem oil and oil extract of *Hypericum* (referred as Mix in FIG. 7) and using meat immersed in water as control;

Biocidal effect of the different substances: water, neem oil, oil extract of *Hypericum*, a 50/50 mix of neem oil and oil extract of *Hypericum* (referred as Mix in FIG. 8) on the larval development of *Calliphora* sp.

Figure 1:
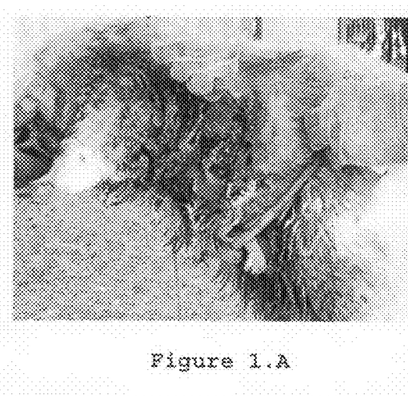
FIGS. 1A and 1B show the aspect of a biting wound on a Maremmano dog at the first day of treatment (FIG. 1A) and after 23 days of treatment (FIG. 1B).
Figure 2:
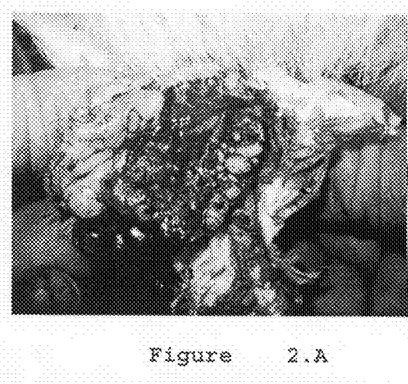
FIGS. 2A and 2B show the aspect of a lesion to the foreskin of a ram colonised by *Wophartia magnifica* maggots at the first day of treatment (FIG. 2A) and after 10 days of treatment (FIG. 2B).
Figure 3:
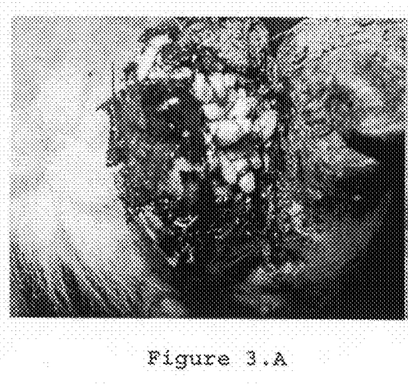
FIGS. 3A and 3B show a sheep hoof infested with *Wolphartia magnifica* maggots at the first day of treatment (FIG. 3A) and after 10 days of treatment (FIG. 3B).
Figure 4:
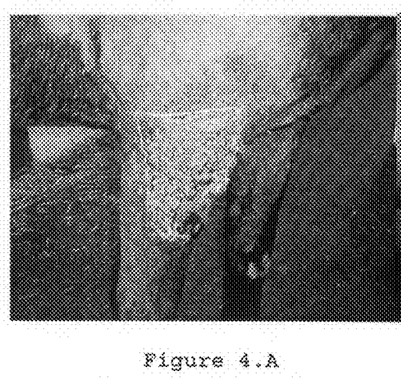
FIGS. 4A and 4B show the aspect of a traumatic skinning wound to the upper part of horse's right leg 20 days after the traumatic event (FIG. 4A) and after 3 months of treatment with the composition object of the present invention (FIG. 4B).
Figure 5:
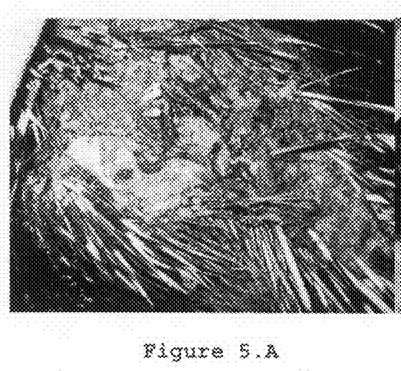
FIGS. 5A and 5B show a hedgehog with lacerated and bruised wounds at the first day of treatment (FIG. 5A) and after 1 month of treatment.
Figure 6:
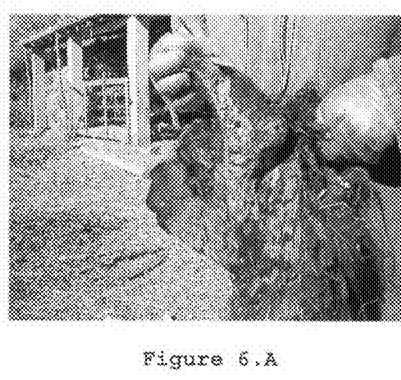
FIGS. 6A and 6B show a purulent lesion due to *Corynebacterium pseudotuberculosis* in alpaca at the first day of treatment (FIG. 6A) and 1 month after treatment (FIG. 6B).
Figure 7:
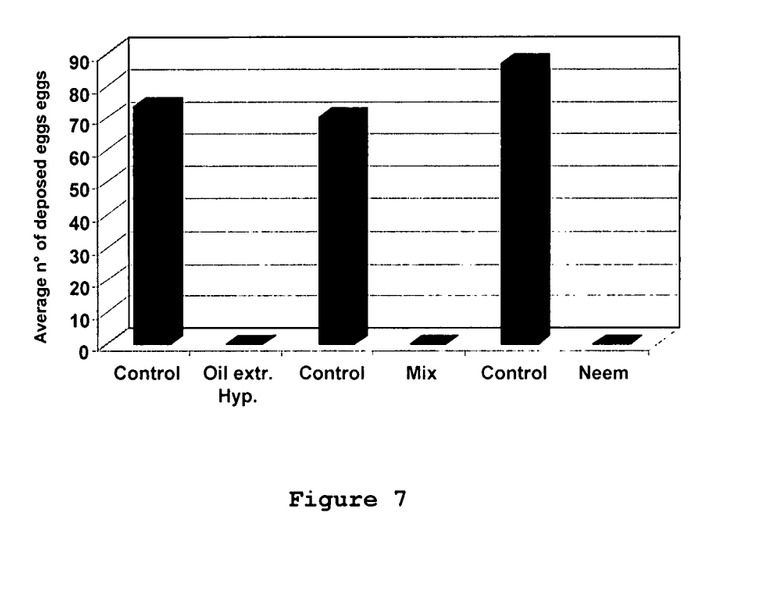
FIG. 7 shows the repellent effect of the different components of the composition against mature female *Callyphora* flies ready to oviposit. The control is meat immersed in water.
Figure 8:
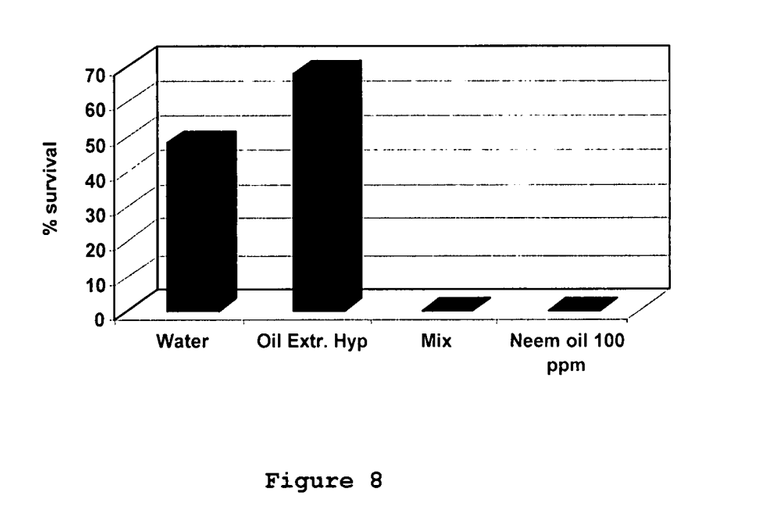
FIG. 8 illustrates the biocidal effects of the different components of the composition against the developing of larvae of *Callyphora* sp.
Figure 9:
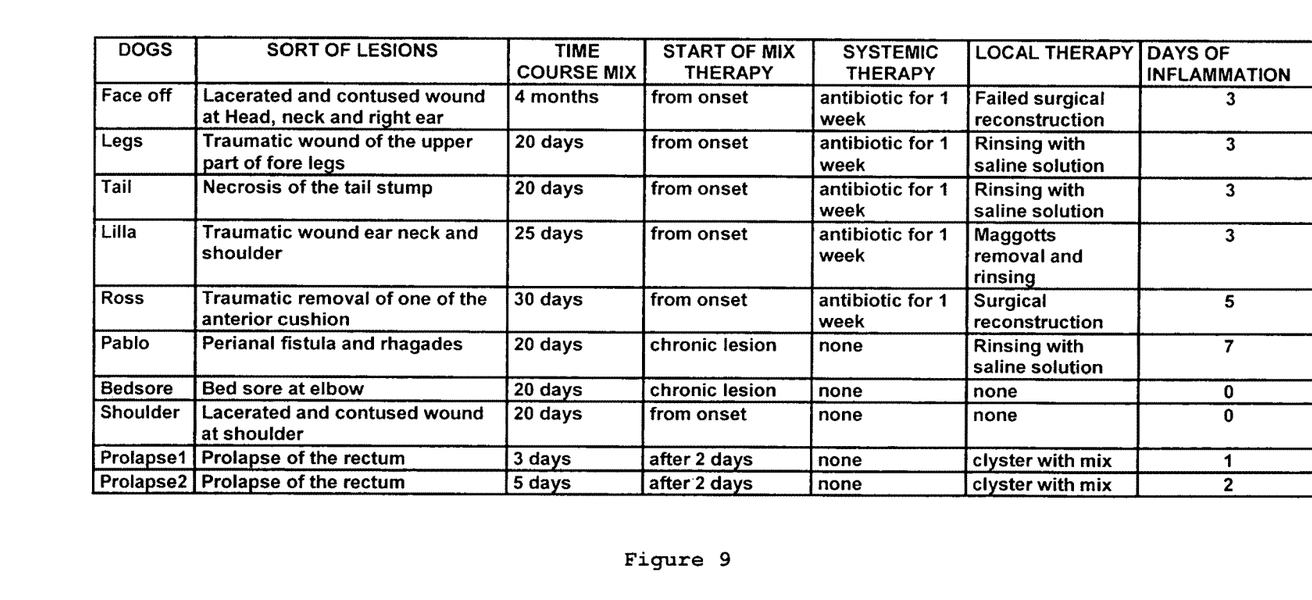
Figure 10:
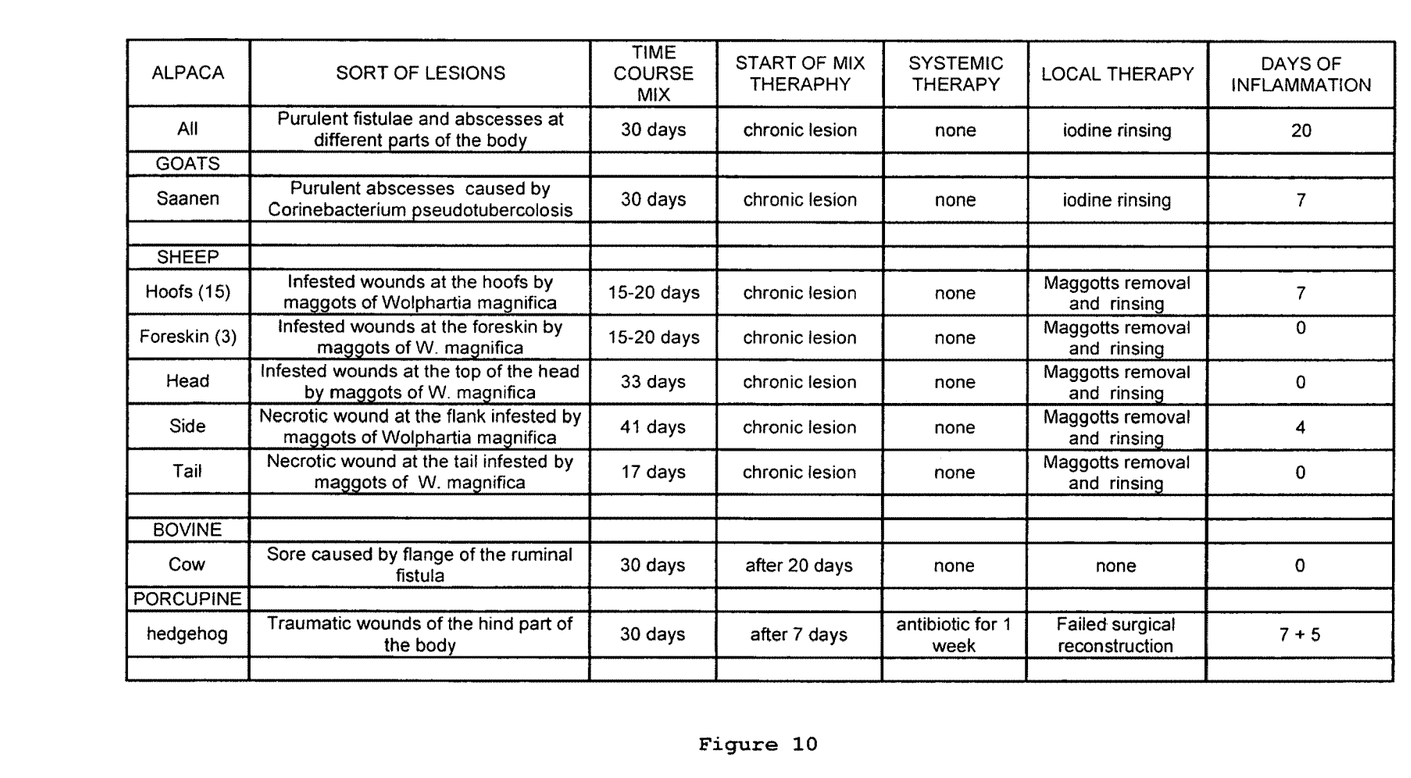

The experimental results shown in FIGS. 7 and 8 clearly indicate that both components have repellent effect versus gravid female *Callyphora* flies like the composition itself. The biocidal effect of the present composition is only due to the neem oil component.

Clinical Experimentation

The clinical experimentation was carried out on various types of lesion of different animals: dogs (FIG. 9), alpaca, goat, sheep, cow, hedgehog (FIG. 10) and horses (FIG. 11).

It has been demonstrated that using the composition, object of the present invention, it is possible to solve the healing of external wounds, of whatever kind and extension, through the speeding up and strengthening of the healing process, without using a local antibiotic treatment, (with exception of a systemic antibiotic treatment to be carried out during the initial phases of the activation of the wounded surface protection given by the granulation tissue) and contemporary conferring a further protection towards myiasigenic flies which may colonise sores or external wounds both in human as in animal, due to its repellent effect.

The healing times are contained and/or reduced to the essential physiological processes typical for each animal species, due to the evident stimulation of the healing processes and due to the avoidance of further complications which usually are present. Therefore it is evident that, especially in veterinary medicine, those subjects used to work can keep on living in their usual environment and fulfil their functions, if no other invalidating conditions subsist.

Special Case: Horses

Of great interest was the clinical experimentation on horses, shown in the table of FIG. 11. In fact, a well-regulated Wound healing process in horses represents the most important goal for equine management. In this species the healing process is slow and often complicated by several pathologies. The most important is cheloid formation.

Cheloid is a disturbance of the granulation tissue due to a hyperproliferation of the fibroblasts. These cells stop the mitogenic activity when enough extracellular matrix fills the wound crater. Collagen fibrils of the matrix start to retract anchoring the wounds edges to fibroblasts. When the collagen fibrils start to retract, fibroblasts stop to secrete the matrix (antimitogenic effect). Most of them undergo apoptosis (cell death without inducing an inflammatory reaction) and quiescence (sleeping fibroblasts), while only a small part undergo the transformation into myofibroblasts (which play a role in the last phases of the wound healing). Newly formed capillary vessels are absorbed and disappear in synchrony with the fibroblasts. Keratinocytes on the top of the healed area start to re-epithelialize the area and the process is complete: In horse, researchers have identified two orders of problems responsible for the high incidence of cheloid pathology: 1) exaggerated tension stimuli at the levels of the distal part of the horses legs, due too scarcity of muscle mass and hypodermal fat and 2) slow capacity of the keratinocytes to obtain the re-epithelialization of the granulated area maybe due to a scarcity of the signals responsible for the antimitogenic effects on fibroblasts. Because tension stimuli exerted at the level of the wound edges, by adjacent healthy skin, disturbs the antimitogenic effects of the matrix retraction, wound localised at the distal part of the horse's limbs, in which skin tension is very strong, undergo cheloid formation. Besides the effects are amplified by the slow rate of keratinocyte proliferation which determines too low levels of antimitogenic keratinocyte derived modulators. The results is that fibroblast do not recognize the antimitogenic effect and continue to proliferate and secrete extra-cellular matrix. Granulation tissue becomes very large, it looks like a soft sponge without showing signs of regression. It is very fragile, bleeds continuously and can provoke serious functional damage because it can trap the anatomical structures inside it (nerves, tendons, etc.). They are very hard to control, time of healing is abnormally prolonged, no effective therapy is actually available. Usual very aggressive therapy consists in burning the exuberant tissue by application of salicylic acid on the cheloid surface, until its level retracts to skin level and re-epithelialization is performed. It is a very time consuming therapy. Using the composition, object of the present invention, without any type of bandage (as in normal use of the present composition) on a wound in the distal part of a horse's limb, in which cheloid is formed, we observe that the therapy with the present composition is not able to control the cheloid formation. If permanent bandaging of the wound is applied without using said composition, cheloid continues to grow, it is possible to observe some autolytic effect on the cheloid surface due to compressive hypoxia, but not cheloid regression. When therapy with the present composition, twice a day, is associated to permanent bandaging of the wounds, we observe an amazing regression of all the pathologic parts of the cheloid.

After 3 days of mixture therapy, exuberant tissue shows pale colour and less thickness. After 5 days the exuberant tissue has completely disappeared without signs of necrosis or presence of debris. Tissue has been absorbed as in the case of physiologic apoptosis. These observations are enforced by the haemorrhagic effect we observe at the bandage removal which lasts no more than two minutes. Bleeding concerns the entire wound surface where cheloids is present. Wound surface presents a normal granulation tissue, the wound's edges show the normal healing process (re-epithelialization). It has been hypothesized that the apoptosis affects only the exuberant fibroblasts, while the vessels are not involved. When the bandage is removed, tracts of the vessels not anymore included in the matrix, start the bleeding. When the composition object of the present invention is used on cheloids, no debris or necrotic tissue are present while when only permanent bandage is applied cheloids do not disappear and some autolytic phenomenon with necrotic debris, are present. The time of healing in the therapy with the present composition is faster than Salicylic acid therapy. Association of permanent bandage with Salicylic acid therapy is not as effective as the therapy with the present composition. These observations make it realistic to manage the worst wounds in horses, without having the problem of cheloid formation. Permanent bandaging associated to the composition, object of the present invention have to be applied to the wounds under cheloid risk until the wounds are completely closed. If the permanent bandage is removed, within six hours, cheloids formation starts again and the process is very fast. Course of new cheloid formation will undergo the same schedule of 5 days of regression and final bleeding phase, before showing a normal granulation tissue when the present composition and permanent bandage are once more applied. Permanent bandage acts by avoiding the tension between the wound edges, but healing process has to be supported by healing factors present in the mixture. Neither permanent bandage nor therapy with the present composition alone can effectively act on cheloids formation, neither other existing therapies alone or associated can avoid cheloids formation or promote the fast resolution shown by the composition object of the present invention.

The invention claimed is:

1. A topical composition for treating external wounds of animals and humans comprising a combination of neem seed oil in an amount of between 10% and 50% and an oil extract of *Hypericum perforatum* in an amount of between 10% and 50%, wherein the oil extract is obtained from macerated flower crowns of *Hypericum perforatum*.

2. The composition according to claim 1, further comprising an added amount of Azadirachtin A.

3. The composition according to claim 2, wherein the added amount of Azadirachtin A is added at a concentration of between 100 ppm and 1000 ppm.

4. The composition according to claim 1, further comprising olive oil.

5. The composition according to claim 1, further comprising essential oils derived from oregano, basil and rosemary as antioxidant and flavoring agents.

6. The composition according to claim 1, further comprising bees wax in a percentage between 7% and 15%.

7. The topical composition according to claim 1, wherein the combination includes about 50 weight percent of each of the neem seed oil and the oil extract of *Hypericum perforatum*.

8. The topical composition according to claim 5, further comprising an added amount of Azadirachtin A at between 100 ppm and 1000 ppm.

9. The topical composition according to claim 6, further comprising an added amount of Azadirachtin A at between 100 ppm and 1000 ppm.

10. The topical composition according to claim 8, wherein the combination includes about 50 weight percent of each of the neem seed oil and the oil extract of *Hypericum perforatum*.

11. The topical composition according to claim 9, wherein the synergistic combination includes about 50 weight percent of each of the neem seed oil and the oil extract of *Hypericum perforatum*.

12. The composition according to claim 10, further comprising bees wax in a percentage between 7% and 15%.

13. The composition according to claim 8, further comprising bees wax in a percentage between 7% and 15%.

14. The composition according to claim 3, further comprising bees wax in a percentage between 7% and 15%.

15. The composition according to claim 13, wherein the synergistic combination includes about 50 weight percent of each of the neem seed oil and the oil extract of *Hypericum perforatum*.

16. The composition according to claim 14, wherein the synergistic combination includes about 50 weight percent of each of the neem seed oil and the oil extract of *Hypericum perforatum*.

17. The topical composition of claim 2, wherein the combined amount of neem seed oil and oil extract of *Hypericum perforatum* includes about 50 weight percent of each.

18. A method for treating external wounds of animals and humans by administering the topical composition according to claim 1.

* * * * *